(12) United States Patent
Long

(10) Patent No.: US 6,435,705 B1
(45) Date of Patent: Aug. 20, 2002

(54) APPARATUS AND METHOD FOR DELIVERING AND MIXING A LIQUID BONE CEMENT COMPONENT WITH A POWDER BONE CEMENT COMPONENT

(75) Inventor: Jack F. Long, Warsaw, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/723,784

(22) Filed: Nov. 28, 2000

Related U.S. Application Data

(63) Continuation-in-part of application No. 09/293,396, filed on Apr. 16, 1999, now Pat. No. 6,296,149, and a continuation-in-part of application No. 09/354,634, filed on Jul. 16, 1999, now Pat. No. 6,254,268.

(51) Int. Cl.⁷ ................................................ B01F 13/06
(52) U.S. Cl. ........................................ 366/139; 366/247
(58) Field of Search ............................ 366/96–98, 130, 366/139, 162.1, 168.1, 189, 241–248, 249–252, 288, 605

(56) References Cited

U.S. PATENT DOCUMENTS

| 261,425 A | 7/1882 | Blair |
|---|---|---|
| 2,305,238 A | 12/1942 | Coates |
| 2,572,375 A | 10/1951 | Oertli |
| 2,732,102 A | 1/1956 | Ekins |
| 2,750,943 A | 6/1956 | Dann |
| 3,029,653 A | 4/1962 | Nilsson |
| 3,141,583 A | 7/1964 | Mapel et al. |
| 3,169,156 A | 2/1965 | Johnson et al. |
| 3,193,146 A | 7/1965 | Isgriggs et al. |
| 3,255,747 A | 6/1966 | Cochran et al. |
| 4,090,639 A | 5/1978 | Campbell et al. |
| 4,338,925 A | 7/1982 | Miller |
| 4,339,058 A | 7/1982 | Wendt |

(List continued on next page.)

FOREIGN PATENT DOCUMENTS

| DE | 29 21 565 | | 12/1980 |
|---|---|---|---|
| DE | 195 32 015 A1 | | 3/1997 |
| EP | 439413 | * | 7/1991 |
| GB | 2187110 | * | 9/1987 |
| WO | WO 84/03830 | | 10/1984 |

Primary Examiner—Charles E. Cooley
(74) Attorney, Agent, or Firm—Maginot, Moore & Bowman

(57) ABSTRACT

A bone cement mixing apparatus for mixing a powder bone cement component with a liquid bone cement component includes a bowl and a lid removably secured to the bowl. The lid has a sealable liquid delivery port defined therein which is adapted to sealingly receive an outlet coupling of a liquid delivery device. The bone cement mixing apparatus also includes a crank rotatably attached to the lid and a blade positioned in the bowl. The blade is secured to the crank such that rotation of the crank causes rotation of the blade. A method for mixing bone cement is also disclosed.

14 Claims, 14 Drawing Sheets

U.S. PATENT DOCUMENTS

| | | |
|---|---|---|
| 4,342,310 A | 8/1982 | Lindmayer et al. |
| 4,356,938 A | 11/1982 | Kayser |
| 4,364,388 A | 12/1982 | Cech |
| 4,406,654 A | 9/1983 | Bristow |
| 4,425,121 A | 1/1984 | Young et al. |
| 4,546,767 A | 10/1985 | Smith |
| 4,569,662 A | 2/1986 | Dragan |
| 4,576,152 A | 3/1986 | Muller et al. |
| 4,619,613 A | 10/1986 | Dragan |
| 4,738,664 A | 4/1988 | Prindle |
| 4,768,955 A | 9/1988 | Hirdes |
| 4,787,893 A | 11/1988 | Villette |
| 4,861,339 A | 8/1989 | Jonischkeit |
| 4,940,294 A | 7/1990 | Foster |
| 4,966,601 A | 10/1990 | Draenert |
| 4,973,334 A | 11/1990 | Ziemann |
| 4,994,065 A | 2/1991 | Gibbs et al. |
| 5,022,563 A | 6/1991 | Marchitto et al. |
| 5,073,033 A | 12/1991 | Klepeis |
| 5,090,816 A | 2/1992 | Socha |
| 5,125,836 A | 6/1992 | Dragan et al. |
| 5,197,635 A | 3/1993 | Chang |
| 5,289,731 A | 3/1994 | Womack |
| 5,304,147 A | 4/1994 | Johnson et al. |
| 5,335,824 A | 8/1994 | Weinstein |
| 5,381,931 A | 1/1995 | Chang |
| 5,431,654 A | 7/1995 | Nic |
| 5,432,645 A | 7/1995 | Terunuma et al. |
| 5,509,578 A | 4/1996 | Livingstone |
| 5,638,997 A | 6/1997 | Hawkins et al. |
| 6,042,262 A | 3/2000 | Hajianpour |
| 6,193,108 B1 | 2/2001 | Lepsius et al. |
| 6,224,253 B1 * | 5/2001 | Dixon |
| 6,296,149 B1 | 10/2001 | Long |

* cited by examiner

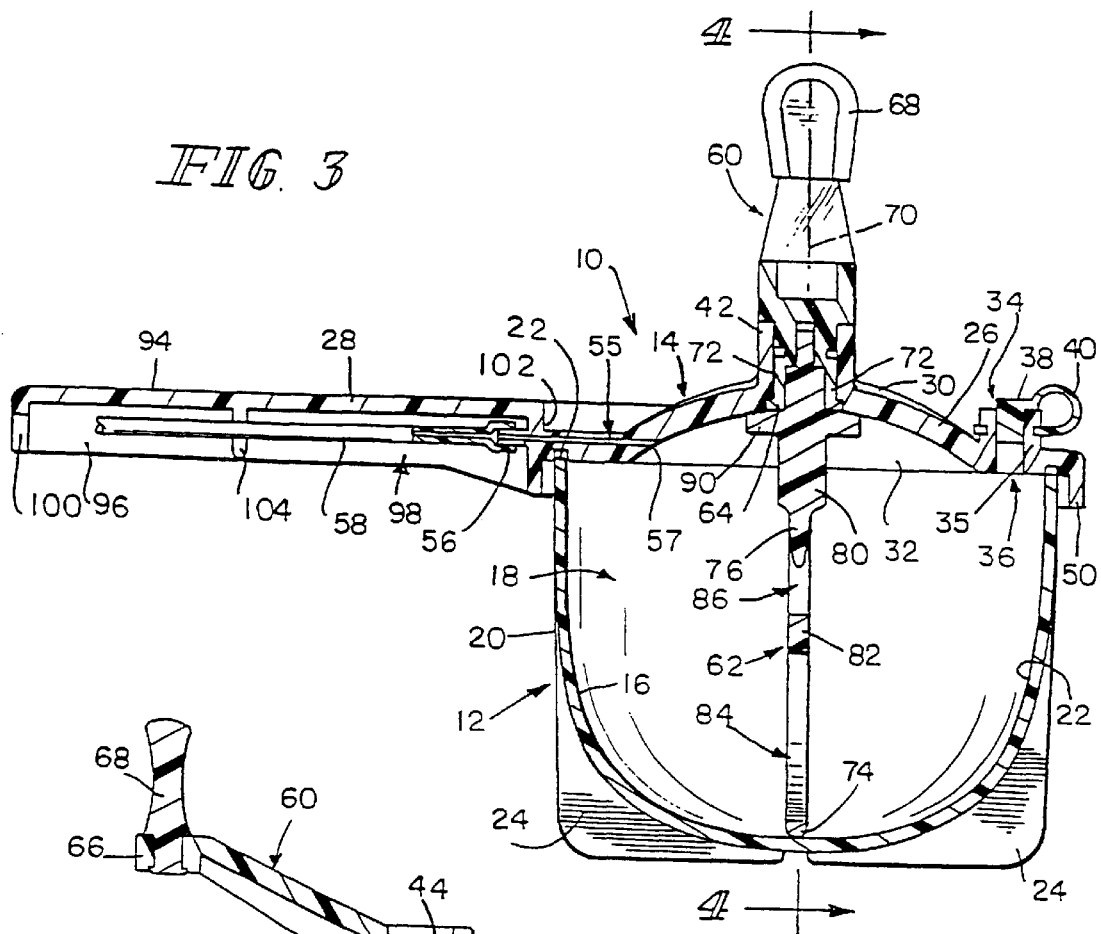

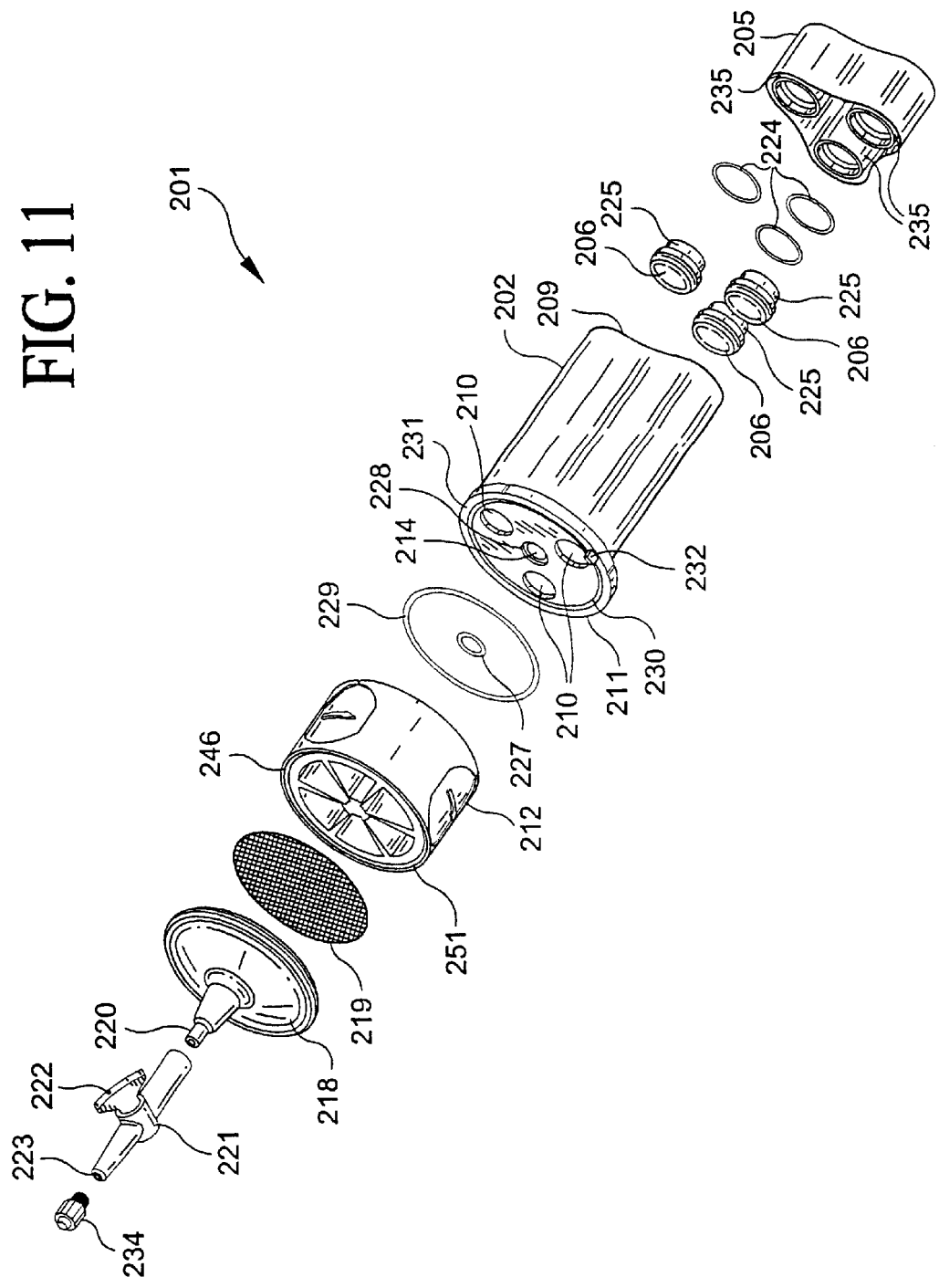

APPARATUS AND METHOD FOR DELIVERING AND MIXING A LIQUID BONE CEMENT COMPONENT WITH A POWDER BONE CEMENT COMPONENT

This application is a continuation-in-part of both U.S. patent application Ser. No. 09/293,396, filed Apr. 16, 1999 entitled "Monomer Delivery Device for Bone Cement Delivery System" by Jack F. Long, now U.S. Pat. No. 6,296,149, and U.S. patent application Ser. No. 09/354,634, filed Jul. 16, 1999 entitled "Bone Cement Mixing Apparatus" by Jack F. Long, now U.S. Pat. No. 6,254,268.

Cross reference is made to U.S. patent application Ser. No. 09/939,812, entitled "Monomer Dispensing Apparatus and Associated Method" by Jack F. Long, which was filed on Aug. 27, 2001, and which is assigned to the same assignee as the present invention.

TECHNICAL FIELD OF THE INVENTION

The present invention relates generally to a surgical assembly, and more particularly to an apparatus and method for delivering and mixing a liquid bone cement component with a powder bone cement component.

BACKGROUND OF THE INVENTION

It is necessary in many orthopedic surgical procedures to employ a cement or grouting type agent, such as for attaching artificial joint implants, repairing or forming joints in bones, or other forms of orthopedic work. The type of cement generally used for these purposes are self-curing resins formed from the blending of a wide variety of liquid monomers or comonomers with powdered polymers or copolymers to form a viscous admixture to be used as the grouting agent.

The admixture of the powder and liquid components develops a quick setting material and preparation of the cement usually occurs directly within the operating theater just prior to use. Monomer vapors, however, are noxious and toxic, and are generated during the depositing of the monomer and when mixing same with bone cement. Because making the bone cement mixture is conducted in the operating room environment, it is important not to allow any monomer or its vapors to escape the monomer delivery device except for deposit into the bone cement mixing system.

What is needed therefore is an apparatus and method for delivering and mixing a liquid bone cement component with a powder bone cement component which overcomes one or more of the above-mentioned drawbacks. What is particularly needed is an apparatus and method for delivering and mixing a liquid bone cement component with a powder bone cement component which reduces, if not eliminates, exposure to vapors from the liquid bone cement component within the operating theater.

SUMMARY OF THE INVENTION

In accordance with one embodiment of the present invention, there is provided an apparatus for preparing bone cement from a powder bone cement component and a liquid bone cement component. The apparatus includes a bowl and a lid removably secured to the bowl. The lid has a sealable liquid delivery port defined therein. The apparatus also includes a crank rotatably attached to the lid and a blade positioned in the bowl. The blade is secured to the crank such that rotation of the crank causes rotation of the blade. The apparatus also includes a monomer delivery device having an outlet coupling which is removably securable to the liquid delivery port of the lid.

In accordance with another embodiment of the present invention, there is provided a surgical assembly for mixing a liquid bone cement component with a powder bone cement component. The surgical assembly includes a mixing device having a bowl, a lid removably secured to the bowl. The lid has a sealable liquid delivery port defined therein. The mixing device also has a crank rotatably attached to the lid, and a blade positioned in the bowl. The blade is secured to the crank such that rotation of the crank causes rotation of the blade. The surgical assembly also includes a liquid delivery device having a liquid storage container for storing the liquid bone cement component, and an outlet coupling sealingly secured to the liquid delivery port of the mixing device. The liquid bone cement is advanced from the liquid storage container of the liquid delivery device into the bowl of the mixing device via a fluid path which includes the outlet coupling and the liquid delivery port.

In accordance with a further embodiment of the present invention, there is provided a method of mixing bone cement with a surgical assembly. The surgical assembly includes a mixing device having a bowl, a lid removably secured to the bowl, a crank rotatably attached to the lid, and a blade positioned in the bowl. The blade is secured to the crank such that rotation of the crank causes rotation of the blade. The surgical assembly also includes a liquid delivery device having a liquid storage container for storing a liquid bone cement component, and an outlet coupling. The method includes the step of advancing the outlet coupling of the liquid delivery device into sealing engagement with a sealable liquid delivery port defined in the lid of the mixing device. The method also includes the step of advancing the liquid bone cement component out of the liquid storage container of the liquid delivery device and into the bowl of the mixing device via a fluid path which includes the outlet coupling of the liquid delivery device and the liquid delivery port of the lid. The outlet coupling advancing step is performed prior to the liquid bone cement component advancing step.

In accordance with yet another embodiment of the present invention, there is provided a bone cement mixing apparatus for mixing a powder bone cement component with a liquid bone cement component. The bone cement mixing apparatus includes a bowl and a lid removably secured to the bowl. The lid has a sealable liquid delivery port defined therein which is configured to sealingly receive an outlet coupling of a liquid delivery device. The bone cement mixing apparatus also includes a crank rotatably attached to the lid and a blade positioned in the bowl. The blade is secured to the crank such that rotation of the crank causes rotation of the blade.

It is therefore an object of the present invention to provide a new and useful apparatus for delivering and mixing a liquid bone cement component with a powder bone cement component.

It is moreover an object of the present invention to provide an improved apparatus for delivering and mixing a liquid bone cement component with a powder bone cement component.

It is a further object of the present invention to provide a new and useful method for delivering and mixing a liquid bone cement component with a powder bone cement component.

It is also an object of the present invention to provide an improved method for delivering and mixing a liquid bone cement component with a powder bone cement component.

It is yet another object of the present invention to provide an apparatus and method for delivering and mixing a liquid bone cement component with a powder bone cement component which reduces, if not eliminates, exposure to vapors from the liquid bone cement component within the operating theater.

The above and other objects, features, and advantages of the present invention will become apparent from the following description and the attached drawings.

BRIEF DESCRIPTION OF THE DRAWINGS

FIG. 3 is a view along lines 3—3 of FIG. 1, showing the cap situated in the delivery port of the body to form a seal between the body and cap and a blade rotatably coupled to the lid;

FIG. 4 is a view along lines 4—4 of FIG. 3, showing the crank sealing coupled to the lid and the blade coupled to the crank and including a vane;

FIG. 11 is an exploded perspective view of the monomer delivery device from FIG. 10, showing the o-rings between the different components of the device, and including a luer lock attached to the end of the valve;

DETAILED DESCRIPTION OF THE INVENTION

Figure 1:
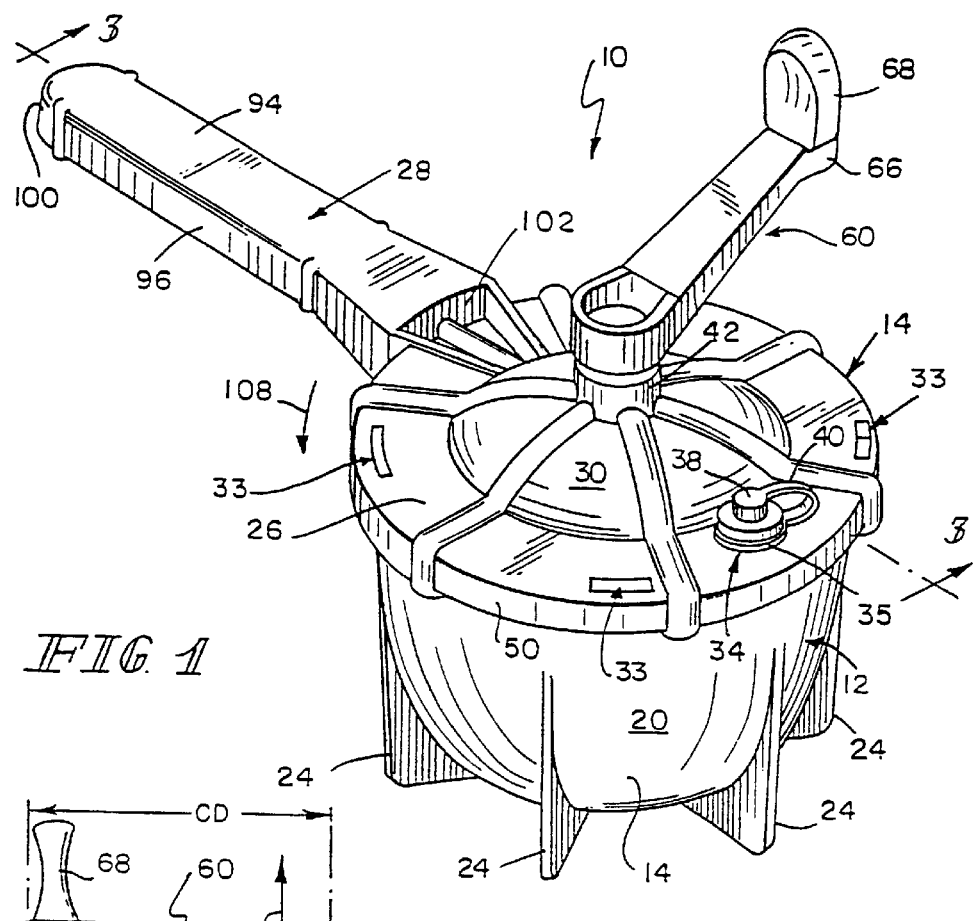
FIG. 1 is a perspective view of bone cement mixing apparatus in accordance with the present invention, showing the apparatus including a bowl, a lid including a luer lock having a body and a cap, and a crank.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 2:
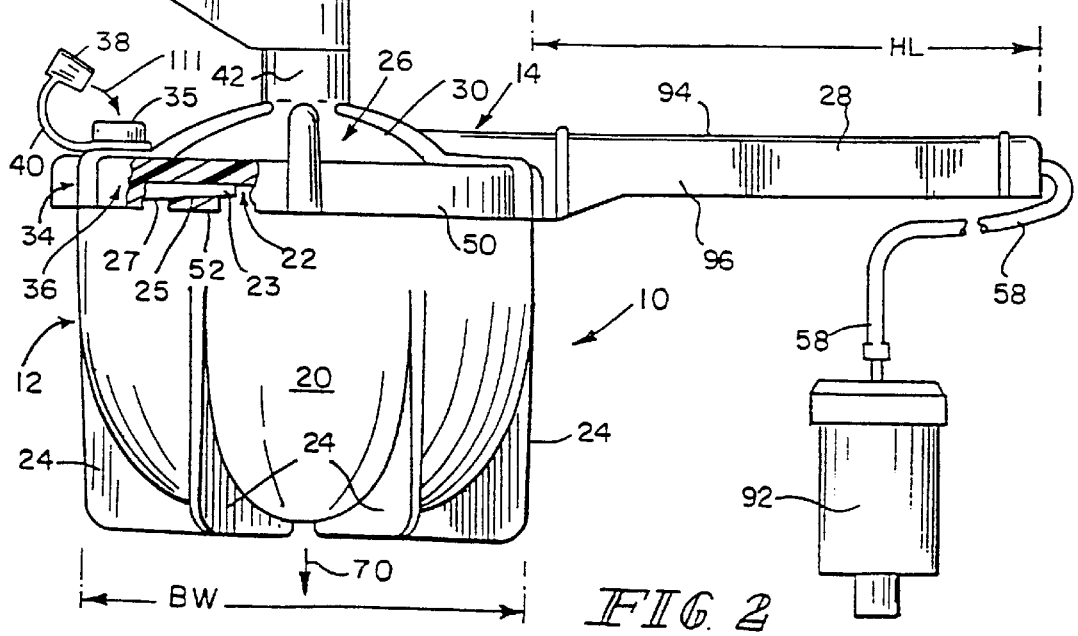
FIG. 2 is a right-side elevation view of the apparatus of FIG. 1, showing the body of the luer lock defining a delivery port, the cap removed from the body, the lid coupled to the bowl by intermittent flanges on the lid fitted under corresponding shims on the bowl, a vacuum tube extending from the lid, and a vacuum pump.

A bone cement mixing apparatus 10 is provided in accordance with the present invention. Mixing apparatus 10 is configured to receive a quantity of bone cement and monomer and mix the cement and monomer under a vacuum. The mixture may then be removed and applied in a prosthesis or deposited in a cement delivery device. As shown in FIGS. 1 and 2, mixing apparatus 10 comprises a bowl 12 and a lid 14 removably secured to bowl 12.

Referring now to FIG. 3, bowl 12 includes an inner surface 16 that defines a cavity 18, an outer surface 20, and an upper rim 22 extending between inner and outer surfaces 16, 18. As shown in FIGS. 2–4, shims 23 extend intermittently about rim 22 of bowl 12. In this embodiment, each shim 23 has a slight depending slope 27 (see FIG. 2) formed at a bottom surface 25 so that as lid 14 engages bottom surface 25, the slope forces lid 14 to make a tighter fit against rim 18. In addition, outer surface 20 is formed to include leg flanges 24 that serve as a stable base.

As shown in FIGS. 1–4, lid 14 covers bowl 12, being sealably and removably securable so that air does not escape between lid 14 and bowl 12. Lid 14, however, is removable so that dry bone cement can be placed into cavity 18 of bowl 12, and the wet bone cement can be removed from cavity 18 after the dry bone cement is mixed with a monomer. Lid 14 includes a lid body or cover 26 and a handle 28 extending from cover 26. The bowl 12 possesses a bowl width BW, and the handle possesses a handle length HL. As shown in FIG. 2, the handle length HL is greater than the bowl width BW.

Cover 26 includes an outer surface 30 and an inner surface 32 facing inner surface 16 of bowl 12. As shown in FIG. 2, a ridge 50 extends about an outer perimeter of cover 26. In addition, several intermittent annular flanges 52 extend radially inward from ridge 50. Thus, when lid 14 is placed over rim 18 of bowl 12 and is rotated, each intermittent flange 52 contacts bottom surface 25 of corresponding shim 23. In addition, slots 33 extend through cover 26 in general alignment with a gasket 54, which extends across slots 33 to prevent air and vapors from leaking therethrough. Gasket 54 is positioned between lid 14 and rim 18, assisting in creating a seal between the two components. It is appreciated, however, that a variety of attachment means can be used to sealably and removably attach lid 14 onto bowl 12. For example, an annular snap fit or threads may be used in place of the annular flange/shim structures. In addition, as shown in FIG. 3, cover is formed to include a vacuum passageway 55 extending therethrough. Vacuum passageway 55, as shown in FIG. 1, includes a vacuum inlet 57 formed through inner surface 32 of cover 26 and a vacuum outlet 56 positioned to lie adjacent to handle 28.

Cover 26 also includes a luer lock 34 and a crank mount 42 extending from outer surface 30 and defining a shaftway 44. Luer lock 34 includes a body 35 that defines a delivery port 36 extending between inner and outer surfaces 32, 30. In addition, luer lock 34 includes a cap 38 that is sized for extension into delivery port 36 and that removably seals body 35 and a tether 40 extending between cap 38 and body 35. Luer lock 34 is configured such that a luer or spout from a monomer delivery device 201 (see FIGS. 10–23) may be extended through delivery port 36 forming a sealing fit with body 35. Thus, luer lock 34 allows monomer to be dispensed into bowl 12 while preventing monomer vapors from escaping between the luer (see FIGS. 10–23) and luer lock 34.

It should be appreciated that the luer lock 34 may be configured to facilitate a "slip fit" type of sealing arrangement, or, alternately, may be configured to facilitate a threaded coupling with the coupling mechanism of the monomer delivery device 201. Moreover, a combination coupling mechanism may be utilized which facilitates mating with both threaded and non-threaded couplings.

Cap 38 is used to seal body 35 after the monomer has been dispensed into bowl 12 and during the mixing process. Cap 38 is shown in a disengaged position in FIG. 2. Cap 38 is removed from body 35 in anticipation of the coupling of the monomer delivery device 201 (see FIGS. 10–25) being inserted in the body 35 for the purpose of delivering monomer from the delivery device 201 into mixing bowl 12. It will be appreciated that a variety of luer locks and luer lock caps may be used in place of luer lock 34. For example, a self-closing luer lock may be used eliminating even the need for luer cap 38 or, as described above, a threaded luer lock may be used to screw cap 38 onto body 35. In another embodiment, the monomer delivery device 201 itself may be used as a seal for the luer lock 34. In yet another embodiment, the luer cap 38 may be replaced with a paper-backed piece of re-sealable tape or the like which can be removed to allow for mating with the delivery device 201, and then replaced when the delivery device 201 is detached.

Figure 6:
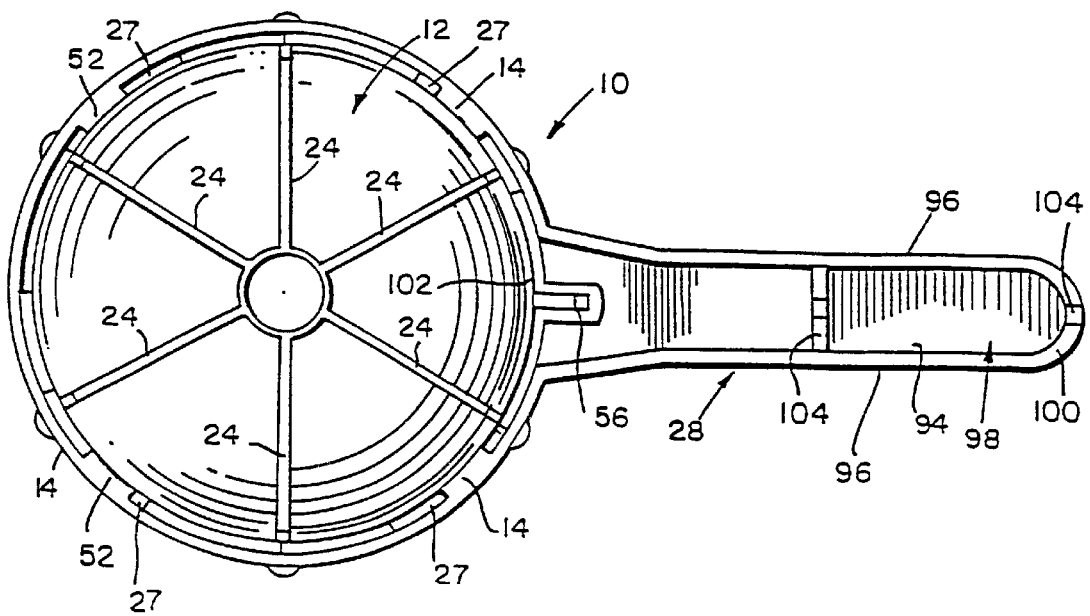
FIG. 6 is a bottom view of the apparatus of FIG. 1 showing the bowl including leg flanges, the lid including a handle having a vacuum outlet and hose grips spaced-apart from the vacuum outlet.

Handle 28 of lid 14 extends from cover 26. In one embodiment, handle 28 serves a dual function. First, as a grippable body for an operator to hold while mixing the bone cement, and second, to provide a conduit for vacuum outlet 56 (see FIGS. 3 and 6) and a vacuum tube 58 (see FIG. 2). It is appreciated, however, that handle 28 may be placed anywhere on mixing apparatus 10. For example, handle 28, in another illustrative embodiment may be attached to bowl 12 (not shown). In addition, vacuum outlet 56 may be disposed through bowl 12. Handle 28 includes a top wall 94, side walls 96, and opposite end walls 100, 102 that cooperate to define a cavity 98 therebetween. In addition, at least one tube grip 104 extends from top wall 94 into cavity 98.

Referring to FIGS. 3 and 4, mixing apparatus 10 includes a crank 60 co-rotatably coupled to lid 14. The crank 60 extends a distance CD in a horizontal direction as shown in FIG. 2. And the handle length HL is greater than the crank distance CD as further shown in FIG. 2. Crank 60 is used by the operator to drive a blade 62 off-set positioned inside bowl 12 and non-concentrically connected to crank 60 to mix the monomer and bone cement together. One end 64 of crank 60 is rotatably extended through shaftway 44, generally at the center of cover 26, while the other end 66 of crank 60 is attached to a knob 68. Crank 60 further includes legs 72 that are sized for rotation in shaftway 44 and are coupled to blade 62. Ultimately, end 64 of crank 60 is coupled to blade 62. Crank 60 is configured to rotate about a longitudinal axis 70 of shaftway 44 which is illustratively the same as the axis of rotation of cover 26. (See FIGS. 3 and 4.) Knob 68 is configured to serve as a grip which the operator may grasp to rotate crank 60 thereby causing blade 62 to rotate. It is appreciated that knob 68 may also be configured to rotatably or fixedly attach to crank 60. In addition, a small o-ring 29 is fitted between legs 72 and crank mount 42 in shaftway 44 to prevent the escape of air or vapor between lid 14 and crank 60.

Figure 5:
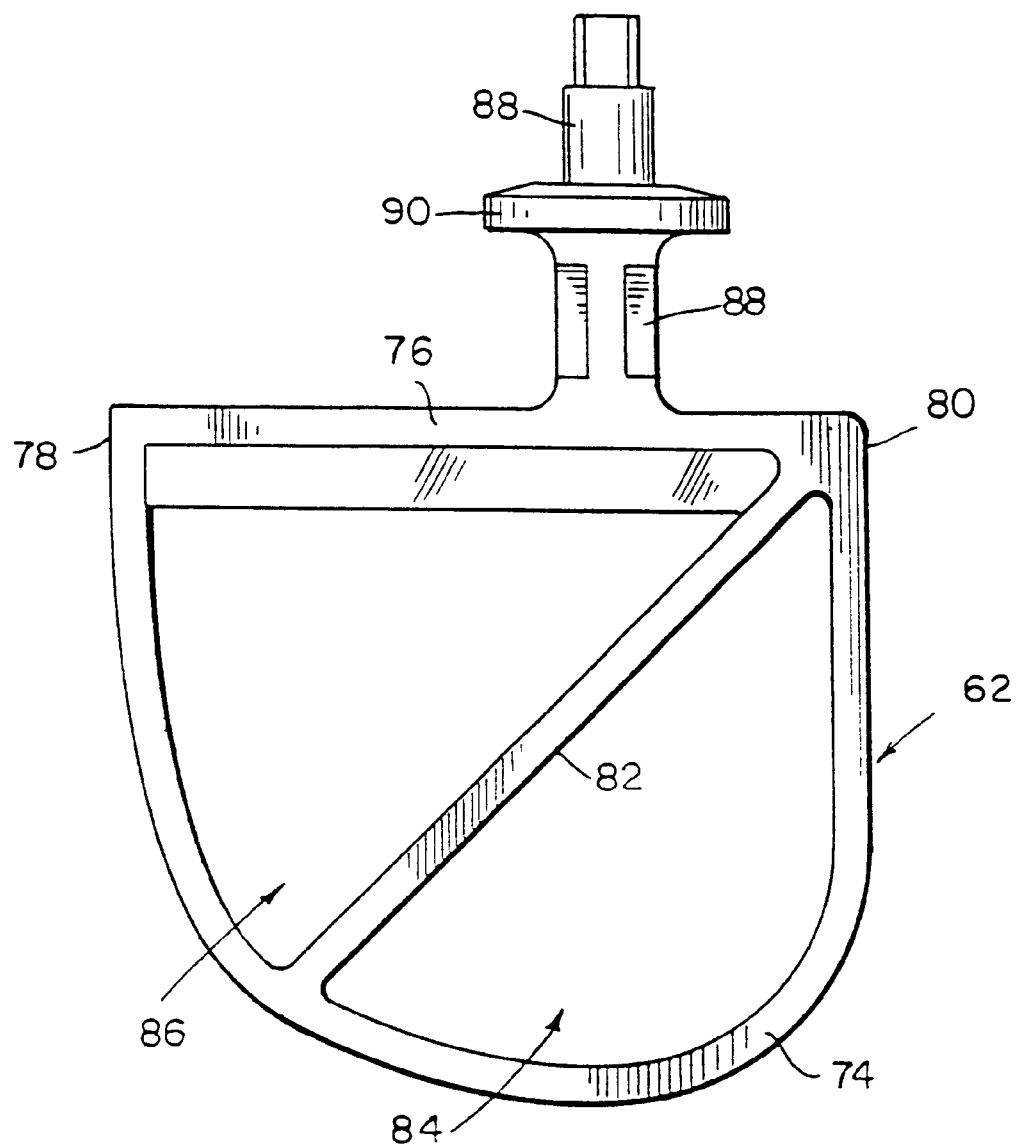
FIG. 5 is a front elevation view of the blade of FIG. 4 showing the blade including a generally U-shaped body, a shoulder blade extending across opposite ends of the body, the vane, a shaft extending from the shoulder blade, and a collar coupled to the shaft.

Rotation of legs 72 of crank 60 rotates blade 62 about longitudinal axis 70 of shaftway 44. As shown in FIGS. 4 and 5, blade 62 includes a generally U-shaped body 74 that has a non-symmetrical extended curved side 120, a generally linear side 122 opposite curved side 120, and a rounded bottom 124 connecting to sides 120, 122, Sides 120, 122 cooperate to define opposite ends 78, 80 of U-shaped body 74. In addition, blade 62 includes a plane top or shoulder blade 76 extending between and connecting opposite ends 78, 80 of body 74 and a vane 82 extending from one of the ends 78 of body 74 to rounded bottom 124 to define a first aperture 84 and a second aperture 86 and to shear and mix the cement nearer the center of bowl 12. In addition, blade 62 includes a shaft 88 that extends from shoulder blade 76 and a collar 90 coupled to shaft 88.

Shaft 88 extends upward from shoulder blade 76 into shaftway 44 and frictionally coupled to depending legs 72. It is understood, however, that the present invention is not limited to only a frictional fit between shaft 88 and crank 60. Any variety of means may connect blade 62 to crank 60, and are contemplated by the present invention. For example, a snap-fit or connectable threads may accomplish the same function. Collar 90 is configured to limit the length with which shaft 88 may extend through shaftway 44. Thus collar engages inner surface 32 of cover 26 to ensure proper placement of blade 62 in cavity 18 of bowl 12. Shaft 88 is also laterally offset from the longitudinal center 106 of blade 62. This offset placement creates additional shearing action per revolution of crank 60. The additional shearing action reduces the amount of mixing required to produce the wet cement.

Because crank 60 rotatably extends through shaftway 44 attaching itself to blade 62, blade 62 rotates as crank 60 is rotated by the operator thereby mixing the monomer with the powder cement inside bowl 12. Referring now to FIG. 4, for optimum mixing, at least a portion of blade 62 passes in close proximity to inner wall 22 of bowl 12 as well as being offset relative to shaft 20. In one embodiment, at least a portion of blade 62 contours about one quarter the circumference of bowl 12 and along a plane generally parallel to longitudinal axis 70 of shaftway 44.

Referring now to FIG. 3, vacuum tube 58 is coupled to vacuum outlet 56. In one illustrative embodiment vacuum tube 58 extends through end wall 102 and into cavity 98 of handle 28 so as not to interfere with the operator as apparatus 10 is being used. Vacuum tube 58 is also connectable to a vacuum pump 92 (see FIG. 2) designed to draw air from mixing apparatus 10 through vacuum outlet 56. Vacuum tube 58 is illustratively secured into place by tube grips 104, which aid in ensuring that vacuum tube 58 remains coupled to vacuum outlet 56.

Figure 7:
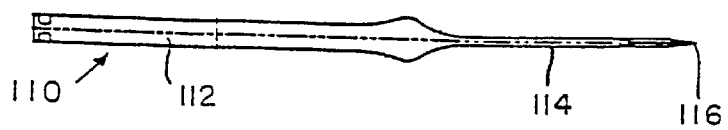
FIG. 7 is a top view of a spatula suitable for use with the apparatus of FIG. 1, showing the spatula including a handle and a blade formed for removing wet bone cement mixture from the bowl.
Figure 8:
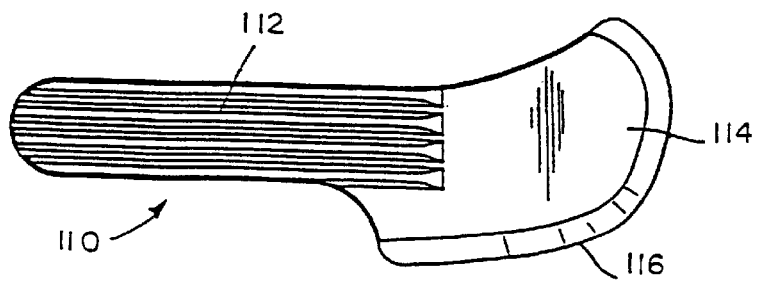
FIG. 8 is a side view of the spatula of FIG. 7.
Figure 9:
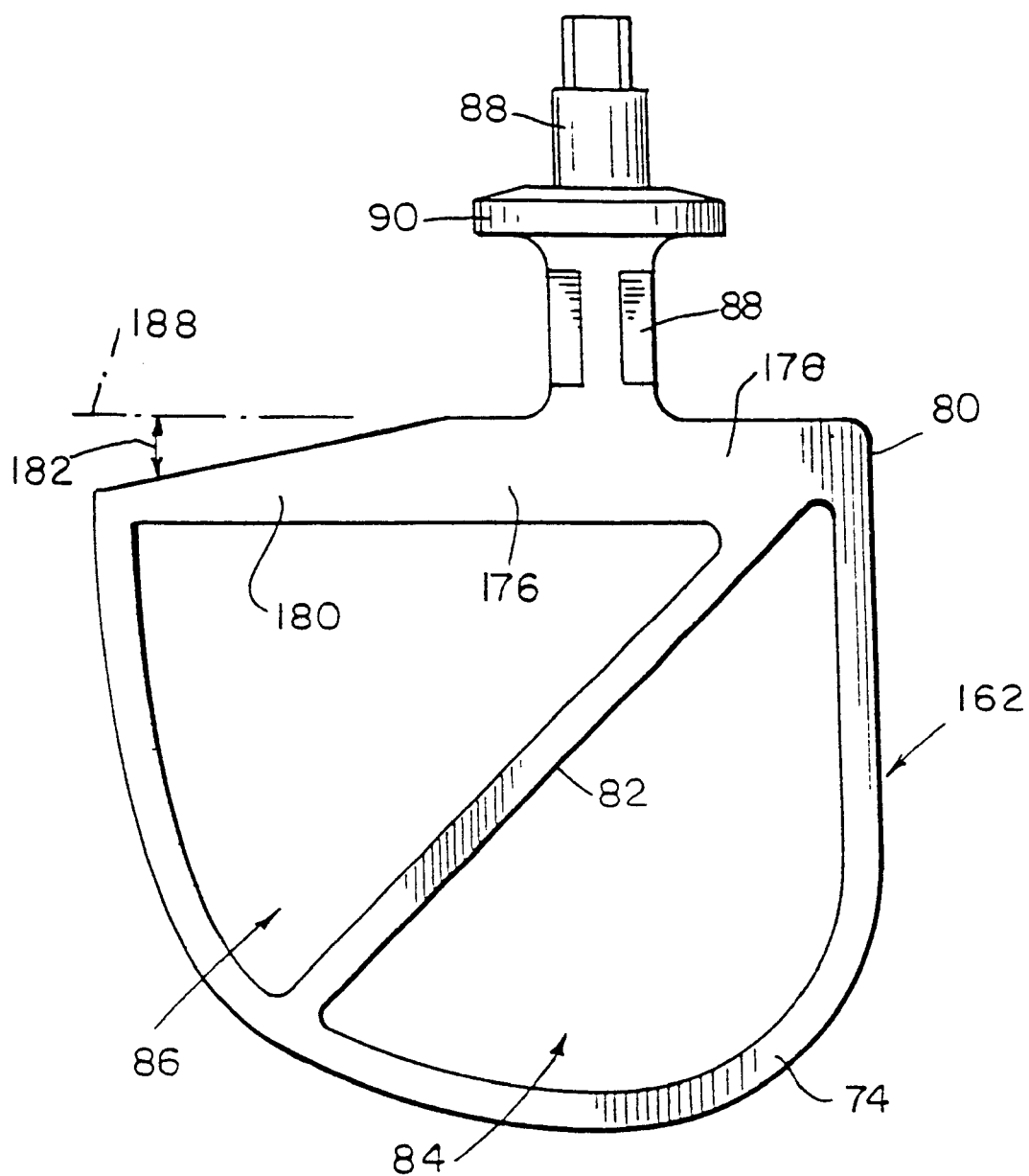
FIG. 9 is a front elevation view of an alternative blade suitable for use with the bowl and lid of FIG. 1, showing the blade including a generally U-shaped body, a tapered shoulder blade extending across opposite ends of the body, a vane extending from the shoulder blade, and a collar coupled to the shaft.

After the monomer and the bone cement are mixed together in mixing apparatus 10, lid 14 is rotated in an opposite direction 108 (see FIG. 1) thereby releasing flanges 52 from shims 23 allowing removal of lid 14 from bowl 12. A spatula 110, as shown in FIGS. 7 and 8, may be used to remove the cement mixture from bowl 12. Spatula 110 includes a handle 112 and a blade 114 coupled to handle 112. Blade 114 is formed to have a curved outer edge 116 that is formed in the partial shape of the contour of inner wall 22. Handle 112 may be gripped by the operator to scoop out the wet cement from cavity 18, using blade 112, for deposit in a cement dispensing device (not shown) or directly onto a prosthetic setting (not shown).

In a further embodiment, blade 162 is provided in accordance with the present invention to be used in place of blade 62. Blade 162 is formed similarly to blade 62 and like reference numerals will be used to denote like components. Blade 162 is formed to include an angled shoulder blade 176. Illustratively, shoulder blade 176 includes a first portion 178 and a second tapered portion 180 that forms an angle generally obtuse from shaft 88. In one illustrative embodiment, the angle of shoulder blade identified by reference number 182 is about −15° relative to horizontal line 188. It is appreciated, however, that the angle of tapered portion 180 may be anywhere above or below horizontal line 188.

For method of manufacture of the wet bone cement mixture, a quantity of bone cement powder is placed in cavity 18 of bowl 12. As shown in FIG. 1, lid 14 is placed over rim 22 and rotated until each flange 52 contacts bottom surface 25 of corresponding shim 23 to press seal 54 against rim 18 and form a seal therebetween. Once lid 14 is sealably attached to bowl 12, monomer may added to the bone cement powder. To prevent the escape of vapors, it is preferable that the monomer be deposited after the cement has already been placed in bowl 12 and lid 14 is coupled to rim 18.

To place monomer in cavity 18, cap 38 is removed from body 35 of luer lock 34. Thereafter, vacuum pump 14 is activated generating a vacuum within bowl 12 to expel air from cavity 18 out through vacuum outlet 56 and tube 58. The vacuum generated in the cavity 18 may be maintained at, for example, about 0.67 to 0.73 bar, just below the boiling point of the monomer creating the maximum vacuum pressure in bowl 12 without the monomer boiling. Illustratively, once the vacuum has begun evacuating the air from cavity 18, the luer or similar structure from the monomer delivery device 201 is inserted into delivery port 36 of body 35 to form a generally sealed connection at which time the monomer may be deposited into bowl 12. The vacuum pump 92 will expel from apparatus 10 any monomer vapors generated by the deposition of the monomer in bowl 12. It should be appreciated that, as described below in greater detail, in certain situations, it may be desirable to introduce the monomer into the bowl 12 without the presence of a vacuum. In any event, after the monomer is deposited into bowl 12, the luer from the monomer delivery device 201 is removed from luer lock 34 and luer cap 38 is immediately fitted into delivery port 36, as shown by arrow 111 in FIG. 2.

After the monomer delivery device 201 is removed from mixing apparatus 10, the operator grips handle 28 with one hand and gripping knob 68 on crank 60 with the other hand. The operator rotates crank 60 about longitudinal axis 70 of shaftway 44. Crank 60 causes body 74 and vane 82 of blade 62 to begin rotating within bowl 12 shearing and mixing the bone cement with the monomer, as previously discussed. An illustrative stirring time for efficient stirring of the mixture is about 45 to 60 seconds. It is preferable that the vacuum remains evacuating vapors from the mixture for about an additional 15 to 20 seconds after mixing has been completed to remove any excess air or monomer vapor from the bone cement mixture. Lid 14 is then rotated on bowl in direction 108 as previously discussed. The operator may then use spatula 110 to scrape the wet bone cement out from bowl 12. The wet bone cement can then be placed into a bone cement dispensing device (not shown) to then be applied to a prosthesis.

As alluded to above, luer lock 34 of cover 26 is configured such that a luer or spout from a monomer delivery device may be extended through delivery port 36 forming a sealing fit with body 35. Thus luer lock 34 allows monomer to be dispensed into bowl 12 while preventing monomer vapors from escaping between the luer and luer lock 34. One such liquid or monomer delivery device is shown in FIGS. 10–23. In particular, a monomer delivery device 201 according to the present invention is part of a bone cement dispensing system for use in a surgical operating room environment. The delivery device 201 is configured to sever an ampule of monomer in a sealed structure and dispense the monomer into another container used for mixing bone cement. The monomer delivery device 201 is sealed to prevent toxic fumes from escaping which could possibly endanger the operator. The following description is but one embodiment of the monomer delivery device, and will be described with reference to FIGS. 10–23.

Figure 10:
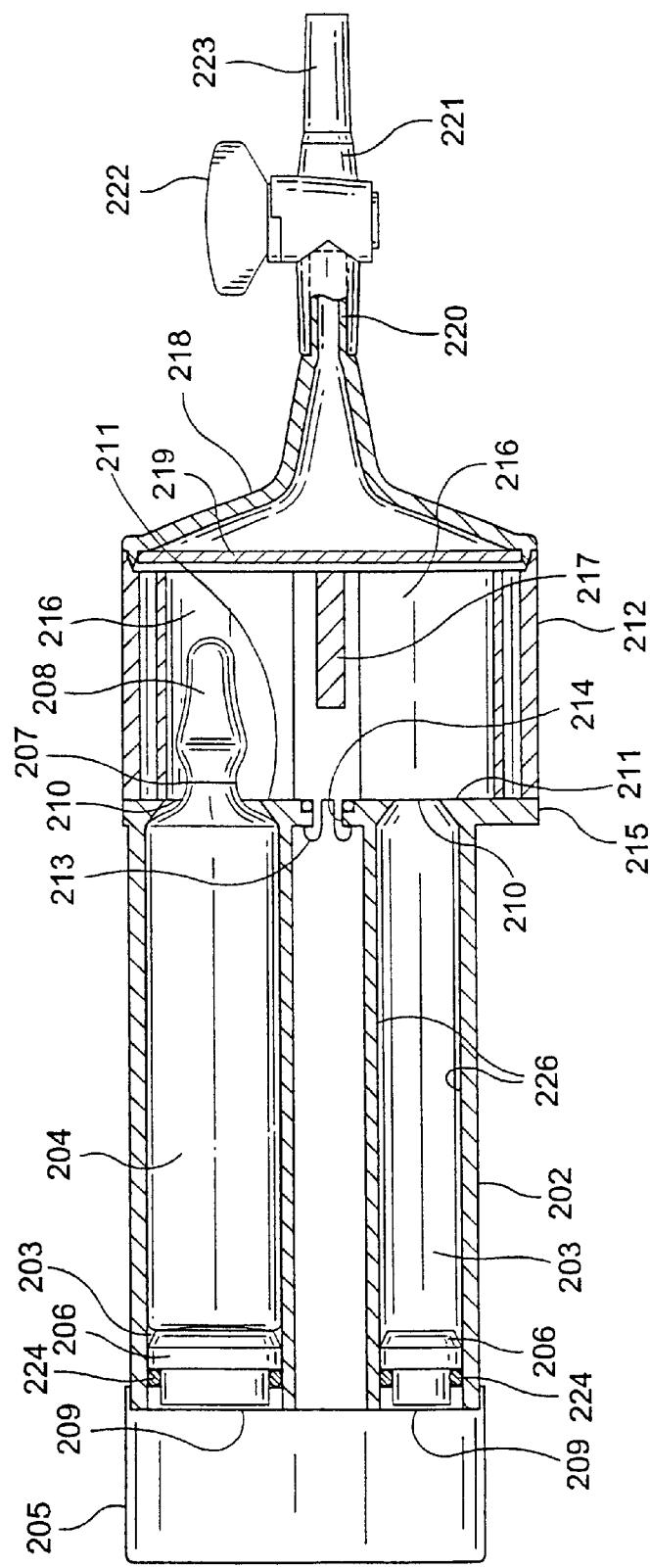
FIG. 10 is a fragmentary cross sectional view of an assembled monomer delivery device embodying the invention showing a body, an end cap, a rotating collar with blades, a funnel, a spout, and a nozzle.
Figure 13:
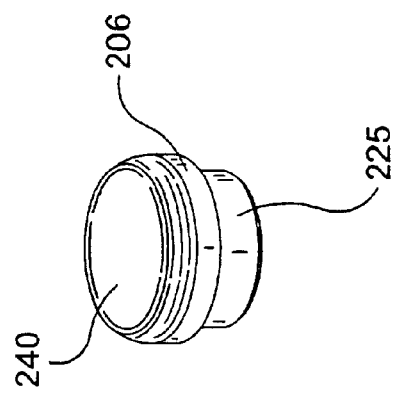
FIG. 13 is a perspective view of a post showing its plug and its top.

A monomer delivery device 201 including a body 202 having an ampule chamber 203 sized to hold an ampule 204 of monomer for deposit to a quantity of bone cement, is shown in FIG. 10. It is understood that body 202 may include one ampule chamber 203 or a plurality of ampule chambers 203. End cap 205 attaches to body 202 after ampule 204 and a post 206 have been inserted into ampule chamber 203. Post 206 includes a plug portion 225 and a top portion 240 (see FIG. 13) and is configured to abut ampule 204 so that ampule 204 is securely contained inside ampule chamber 203. It will be appreciated that the number of posts 206 that can be fitted into body 202 may correspond with the number of ampule chambers 203. It will also be appreciated that closures other than illustrated posts 206 may be used to securely hold ampule 204 in chamber 203.

One illustrated embodiment of ampule 204 may have a neck 207 on one end having an ampule cap 208 attached thereto. A liquid bone cement component such as monomer liquid is encapsulated inside ampule 204. Ampule 204 is placed inside ampule chamber 203 from load end 209 such that ampule cap 208 extends through an aperture 210 on cap end 211 of body 202. A collar 212 is rotatably attached to body 202 by a collar lock 213 to depend from the longitudinal axis of collar 212, and to extend through a collar lock aperture 214 also located on cap end 211. Collar 212 is movable about the longitudinal axis of body 202. A flange 215 is located on cap end 211 having substantially the same diameter as collar 212 and placed adjacent to collar 212 creating a seal.

Collar 212 illustratively has a plurality of broad flat bodies or blades having a length that extends along the longitudinal axis of collar 212 and are sufficiently rigid to sever ampule 204. In one embodiment shown in FIG. 10, the blade lengths alternate from a full depending blade 216 to a half depending blade 217. In this embodiment, half blade 217 depends about half the length of full blade 216 beginning opposite cap end 211 and extending the longitudinal axis of collar 212 (see also FIG. 16). As collar 212 rotates, half blade 217 contacts the tip of cap 208 on ampule 204 causing a shearing force on neck 207 resulting in the shear fracture of ampule at neck 207. Cap 208 is then completely broken and pushed away from ampule 204 by full blade 216. This allows monomer to flow from ampule 204 to collar 212 and eventually out of delivery device 201. It is understood, however, that collar 212 may comprise any type, number, or configuration of blades so long as the blades are able to sever ampule 204. For example, collar 212 may comprise of one large blade, or a plurality of depending full blades.

Illustratively located between collar 212 and funnel 218 is a screen 219 to trap broken particles from ampule 204 in collar 212. The liquid monomer passes through screen 219 into funnel 218. At the end of funnel 218 opposite screen 219 is a spout 220. As shall be discussed below in greater detail, liquid monomer travels from funnel 218 out through spout 220 into the mixing apparatus 10 to be combined with the powder bone cement component. The monomer can either be deposited and combined with the bone cement directly from spout 220, or, in one illustrative embodiment, the monomer can be deposited into a sealable valve 221 that attaches to spout 220. Valve 221 includes a valve closure 222 that allows the monomer to flow out of a valve hole 223 at the discretion of the operator when closure 222 is disengaged, and prevents the monomer from flowing out of valve hole 223 when closure 222 is engaged.

An exploded perspective view of monomer delivery device 201 is shown in FIG. 11. When device 201 is assembled, orings are placed between major components to keep the monomer and the monomer vapor encapsulated inside device 201 and only released through valve hole 223. A medium o-ring 224 is circumferentially fitted around plug 225 (see FIG. 13) of post 206 behind abutting inner wall 226 (see FIGS. 10, 13, and 15) of ampule chamber 203. As post 206 is inserted into ampule chamber 203, medium o-ring 224 creates a seal between post 206 and inner wall 226 preventing any vapors from escaping at that joint (see FIG. 10). Because ampules 204 can be of varied lengths, post 206 can travel linearly along inner chamber 203 to securely hold ampule 204.

A small o-ring 227 may be placed between collar latch 213 (see FIG. 10) and collar latch aperture 214. Small o-ring 227 may be circumferentially fitted around collar latch 213 and seated in an o-ring groove 228, which itself is circumferentially formed on latch aperture 214. This creates a seal between collar latch 213 and collar latch aperture 214.

A large o-ring 229 may be placed between collar 212 and body 202. Large o-ring 229 may be fitted circumferentially around body 202 in a groove 230 near flange 231. When collar 212 is attached to body 202, both small o-ring 227 and large o-ring 229 seal any gaps between collar 212 and body 202 so no monomer vapors or liquid can escape.

Figure 17:
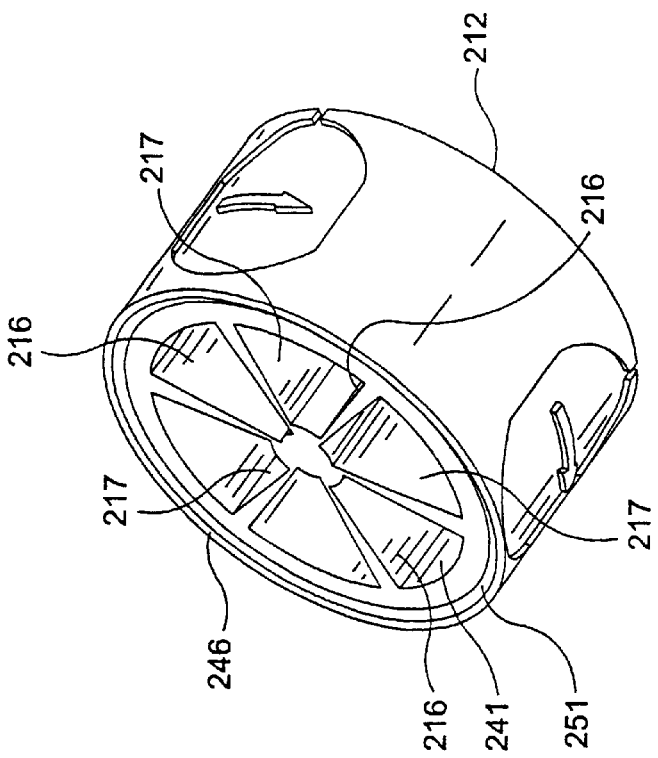
FIG. 17 is a rear perspective view of a portion of the monomer delivery device from FIG. 11, showing the rotating collar having the plurality of half blades and full blades, a collar lock depending from the convergence of the blades, and a tab groove formed inside the collar about the circumference of the bottom end.

A tab 232 is illustratively shown in FIG. 11, extending from flange 231 on cap end 211 of body 202. Tab 232 cooperates with a tab groove 233 (see FIG. 17) in collar 212 to limit collar 212 to a predefined, range of movement about a portion of the collar's circumference. As shown in FIG. 17, tab groove 233 is formed within a portion of the circumference of bottom end 242. Tab groove 233 is approximately one quarter the circumference of collar 212. When collar 212 is pivotally attached to body 202, tab 232 extends from flange 231, and is fitted into tab groove 233. This restricted movement allows only a limited number of blades to sever a particular ampule cap 208 and once tab 232 abuts the end of groove 233, the blades are positioned such that they are not inadvertently covering the severed ampule restricting the flow of monomer. It is understood, however, that collar 212 and the blades 216 and 217 may be configured to sever ampule 204 in a variety of ways; for example, the collar may rotate in a completely, 360 degree circumference about the longitudinal axis, or, the collar may be moved axially inward along the longitudinal axis.

An outlet coupling such as a luer lock 234 (see FIG. 11), is configured to attach to valve 221 and then mate with a luer on the mixing apparatus 10. As shall be discussed below in greater detail, luer lock 234 provides a seal between the monomer delivery device 201 and the mixing apparatus 10 thereby preventing toxic vapors from escaping into the atmosphere at this connection. Monomer delivery device 201, therefore, creates a closed system in which the monomer can safely be added to the bone cement.

Monomer delivery device 201 can be made from a variety of materials. Components from device 201 can be made from most types of plastic, glass, metal, or combinations thereof. One preferred embodiment of device 201 is that it be disposable. Plastic materials like polypropylene or polyethylene are preferable so that after device 201 has deposited the monomer it can be discarded. Because no components of device 201 are disassembled, no residual monomer or vapors will escape. It may be preferable, however, to use a plastic material that will not degrade if it comes into contact with a ketone. Plastics like polycarbonate will work, even though it will eventually degrade when in contact with the monomer, as long as the monomer is dispensed and the device 201 is discarded immediately after severing the ampule 204.

Figure 12:
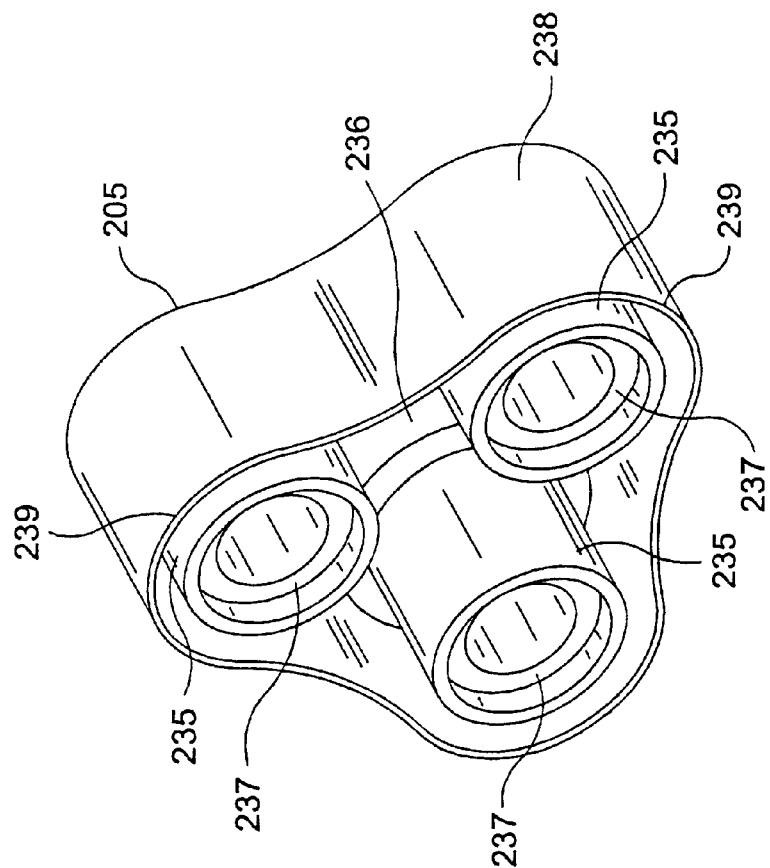
FIG. 12 is a perspective view of a portion of FIG. 11, showing the end cap having a base, post apertures, post stops, an edging attached to the base and a rim attached to the edging.

A perspective view of illustrative end cap 205 is shown in FIG. 12. End cap 205 comprises a post aperture 235. Monomer delivery device 201 can comprise a plurality of ampule chambers 203 (see FIG. 15). End cap 205 will, therefore, be configured with the same number of post apertures 235 as number of aperture chambers 203 provided in body 202 with the shape and size of end cap 205 to conform accordingly. In one illustrative embodiment, post aperture 235 is a cylindrical structure extending from base 236. On the end of post aperture 235 opposite from base 236, a post stop 237 is circumferentially formed around the inner circumference of post aperture 235. Post stop 237 limits the size of the encapsulated portion of ampule chamber 203 by limiting range of movement of post 206. Post stop 237 also prevents post 206 from being pushed out of ampule chamber 203 thereby breaking the seal between post 206 and inner wall 226 (see FIG. 1 0). In addition, an object can extended through end cap 205 and post aperture 235 to push against post 206 thereby securing ampule 204 as previously discussed.

End cap 205 also comprises an edging 238 extending from base 236 and surrounding post aperture 235 contouring the outer perimeter of load end 209 of body 202 (see FIG. 12). Opposite base 236, on edging 238 is a rim 239. Rim 239 attaches to load end 209 after ampule 204 and posts 206 have been inserted into ampule chambers 203. In one embodiment end cap 205 attaches to load end 209 of body 202 by press fitting rim 239 into body 202. In an alternative embodiment, rim 239 can attach to body 202, after ampules 204 have been inserted into ampule chamber 203, using an adhesive, ultrasonic welding or snap-fit.

Figure 14:
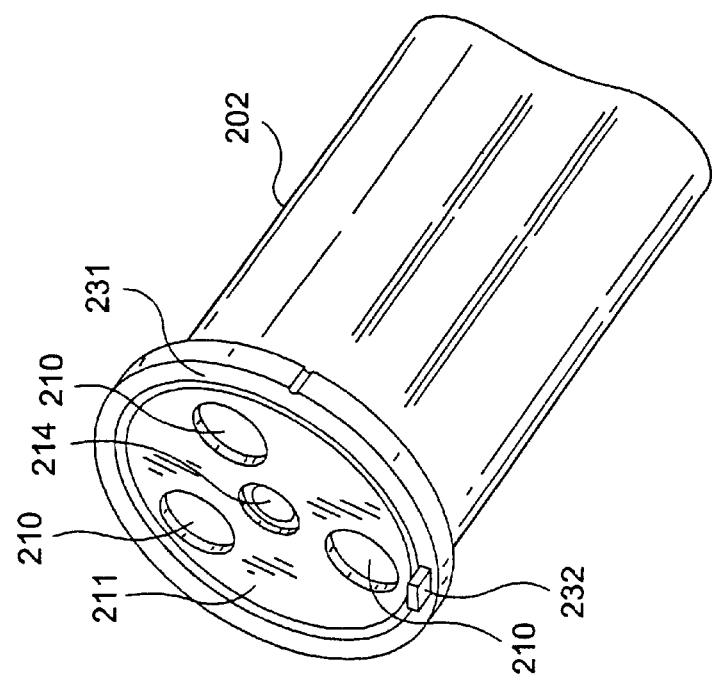
FIG. 14 is a front perspective view of a portion of the monomer delivery device from FIG. 11, showing the body having a plurality of apertures, a collar aperture and a flange.
Figure 16:
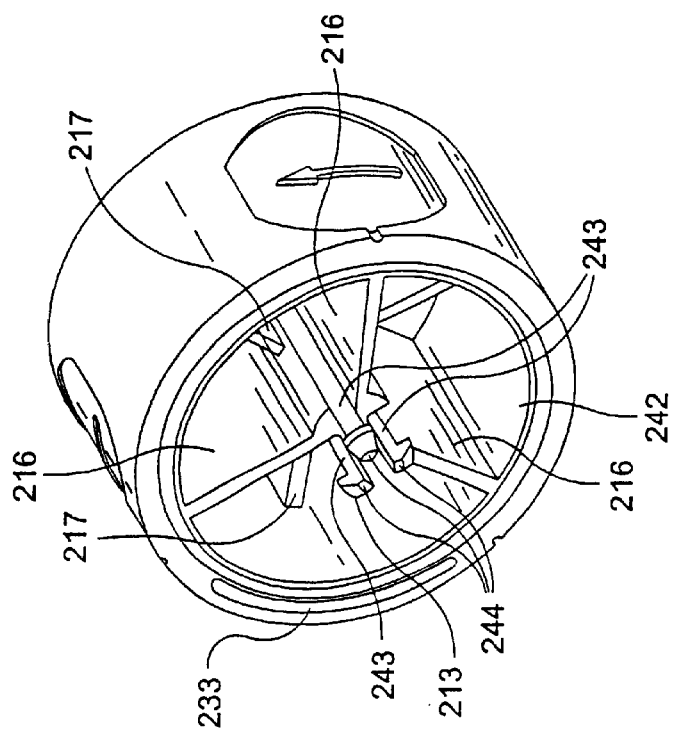
FIG. 16 is a front perspective view of a portion of the monomer delivery device from FIG. 11, showing the rotating collar having a plurality of half blades and full blades.

A front perspective view of body 202 is shown in FIG. 14. Cap end 211 comprises a plurality of apertures 210 disposed therethrough. Each one of a plurality of apertures 210 are axially aligned along the longitudinal axis of each of a plurality of ampule chambers 203, and in tandem arrangement with same. Each aperture 210 is sized to receive extending ampule cap 208 but prevent ampule 204 itself from extending therethrough. As also shown in FIG. 16, one preferred embodiment comprises collar aperture 214 disposed through generally the center of cap end 211.

Figure 15:
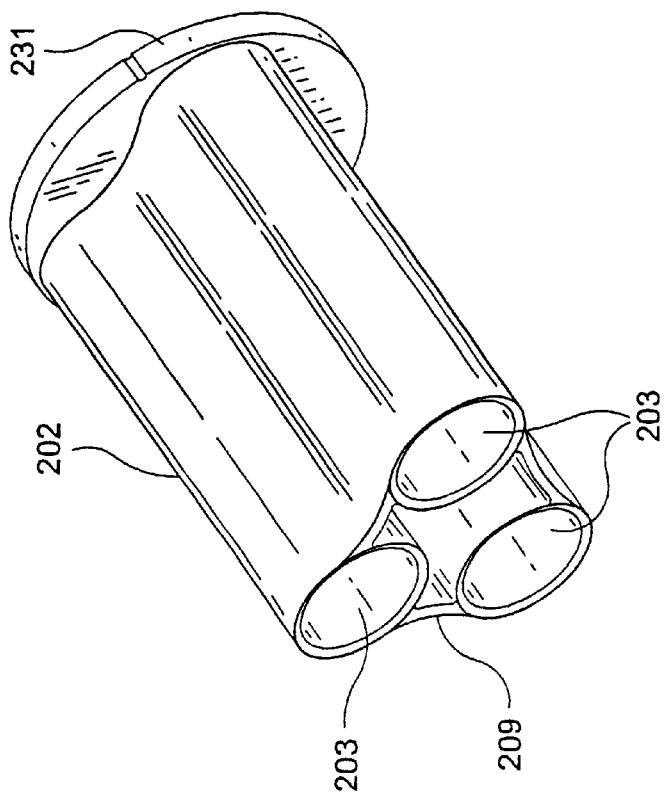
FIG. 15 is a rear perspective view of a portion of the monomer delivery device from FIG. 11, showing the body having a load end and a cap end, a plurality of ampule chambers and the flange.

A rear perspective view of body 202 is shown in FIG. 15, having a plurality of ampule chambers 203 accessible at load end 209. Ampules 204 are loaded from load end 209 and positioned through chamber 203 until ampule cap 208 is extended through aperture 210 as previously discussed. After ampule 204 is loaded into ampule chamber 203, post 206 with medium o-ring 224 attached, is placed inside ampule chamber 203 to seal load end 209. Finally, end cap 205 is attached to load end 209 of body 202 in a manner previously discussed (see FIG. 10).

Figure 18:
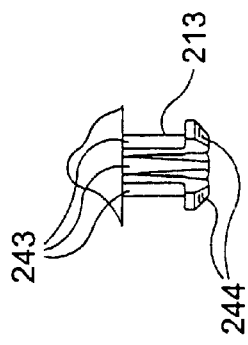
FIG. 18 is a fragmentary side elevation view of a portion of the monomer delivery device from FIG. 10, showing the collar lock.
Figure 23:
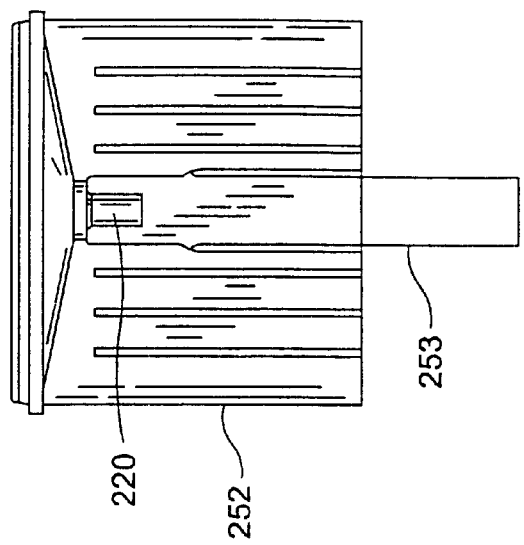
FIG. 23 is a side view of the funnel and guide from FIG. 22 showing an extended spout attached to the funnel.

A side elevation view of collar lock 213 is shown in FIG. 18. Collar lock 213 comprises a plurality of depending prongs 243, with protruding tongues 244 extending from the end thereof. Small o-ring 227 is placed around the plurality of prongs 243 (see FIG. 10). Collar lock 213 then extends through collar lock aperture 214 on body 202 (see FIGS. 10 and 11). Together, prongs 243 create substantially the same diameter as collar aperture 214. However, prongs 243 are sufficiently bendable, yet sufficiently elastic at the same time, and have tongues 244 so configured that collar lock 213 can compress to fit through collar lock aperture 214 and return to its original shape. Tongues 244 then extend past the thickness of collar aperture 214 thereby rotatably securing collar 212 to body 202. It is understood that collar lock 213 can be configured in any manner that rotatably attaches collar 212 to body 202. For example, rather than using three small bendable prongs, two larger bendable prongs might be used, or simply one compressible prong or equivalent structure. Or a still further example, collar 212 may movably snap fit about cap end 211 of body 202. With large o-ring 229 fitted into groove 230, and small o-ring 227 fitted into groove 228, a seal is created between collar 212 and body 202 as previously discussed (see FIG. 11).

Figure 19:
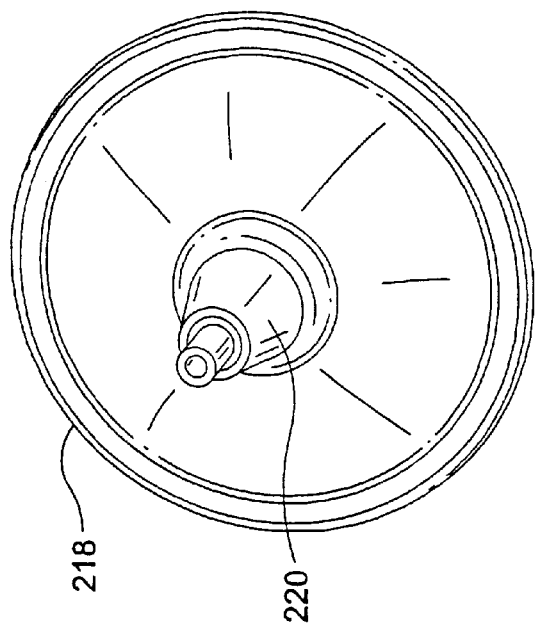
FIG. 19 is a front perspective view of a portion of the monomer delivery device from FIG. 10, showing the funnel.

A front perspective view of funnel 218 is shown in FIG. 19. Funnel 218 has a conically shaped body concluding at spout 220. The conical shape of funnel 218 at spout 220, in this embodiment, is steeper than at the outer edge of funnel 218. It is understood that funnel 218 can have any conical shape, or even none at all, or have a variable conical shape as it concludes to spout 220. In addition, another embodiment of the present invention can have a spout 220 located anywhere on funnel 218. Also, as illustratively shown in FIG. 20, a step structure 245 that attaches funnel 218 to collar 212. Around the circumference of top surface 241 of collar 212 is a ridge 246 as shown in FIG. 16. Ridge 246 corresponds to stepped structure 245 creating a seal between collar 212 and funnel 218 when ultrasonic welded together. It is understood that collar 212 and funnel 218 can be attached by various other means including adhesive, press fit or snap-lock.

Figure 20:
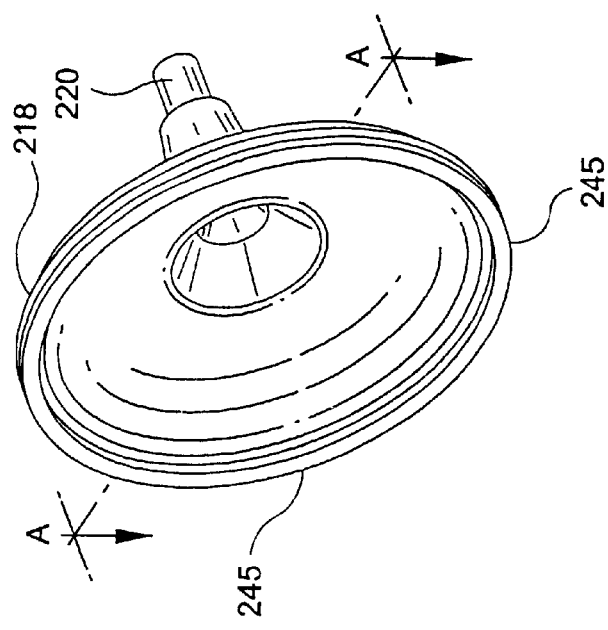
FIG. 20 is a rear perspective view of the funnel from FIG. 19, showing the spout and the step structure.
Figure 21:
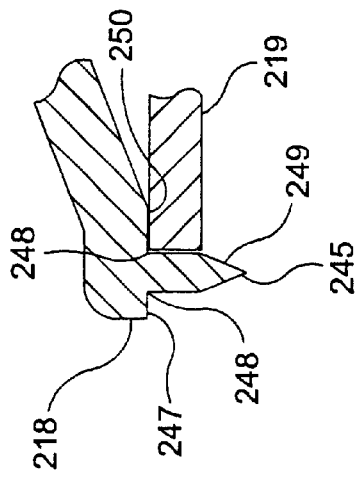
FIG. 21 is a fragmentary cross sectional view of the funnel from FIG. 20, showing the stepped structure taken along cross section A-A in FIG. 20.

A cross sectional view of funnel 218 along line A—A of FIG. 20, is shown in FIG. 21, illustrating the detail of step structure 245. Step structure 245 comprises a narrowly portioned ledge 247 along the outer perimeter of funnel 218. Step 248 forms a thicker portioned tongue 249 with another step 247 forming a narrowly portioned screen ledge 250. When funnel 218 is attached to collar 212, ledge 247 is placed on ridge 246 from collar 212 as previously discussed. Tongue 249 is fitted into tongue groove 251 in collar 212, with screen 219 placed between surface end 241 of collar 212 and screen ridge 250. It is understood that screen 219 is not limited to a particular material or to the traditional weave netting configuration. Screen 219 merely prevents any material from traveling past collar 212. For example, screen 219 can be a porous material filter, or a randomly directional strand mesh.

Figure 22:
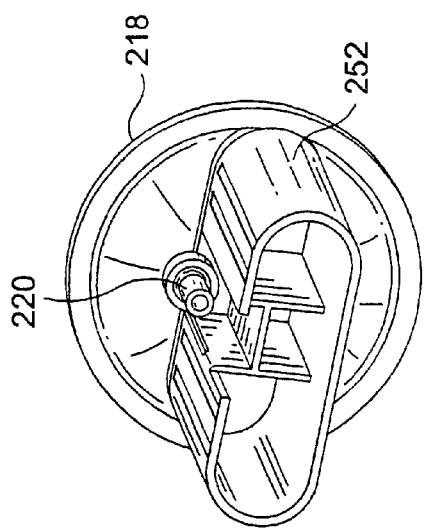
FIG. 22 is a perspective view of the funnel from FIG. 20, showing a guide located near the spout.

Funnel 218 is shown in FIG. 22 having guide 252 located near the spout 220. Guide 252 is used for certain types of cement mixing devices (not shown). An extended spout is shown in a side view of funnel 218 and guide 252 in FIG. 23. Extended spout 253, used in cooperation with guide 252 is specifically suited for dispensing monomer in longitudinal-type cement mixers (not shown). In another embodiment (not shown), extended spout 253 may be fitted to valve 221 thereby extending the valve so it may fit either into a differently configured bone cement mixing bowl, into luer lock 234 that mates with the bone cement mixing bowl.

OPERATION OF THE PRESENT INVENTION

In operation, the bone cement mixing apparatus 10 and the monomer delivery device 201 of the present invention are utilized to delivery and mix a liquid bone cement component with a powder bone cement component during performance of a surgical procedure. In order to do so, the powder bone cement component is first placed in the bowl 12 of the mixing apparatus 10. In particular, the lid 14 of the mixing apparatus 10 is first removed so as to expose the cavity 18 of the bowl 12. Thereafter, a quantity of the powder bone cement component is poured or otherwise advanced into the cavity 18 of the bowl 12.

Once the powder bone cement component has been placed in the bowl 12, the lid 14 is re-secured to the bowl 12. In particular, as shown in FIG. 1, the lid 14 is placed over the rim 22 and rotated until each of the flanges 52 contacts the bottom surface 25 of a corresponding shim 23 to press the seal 54 against the rim 18 thereby forming a seal therebetween. Once the lid 14 is sealably secured to the bowl 12 in such a manner, monomer may added to the bone cement powder.

Figure 24:
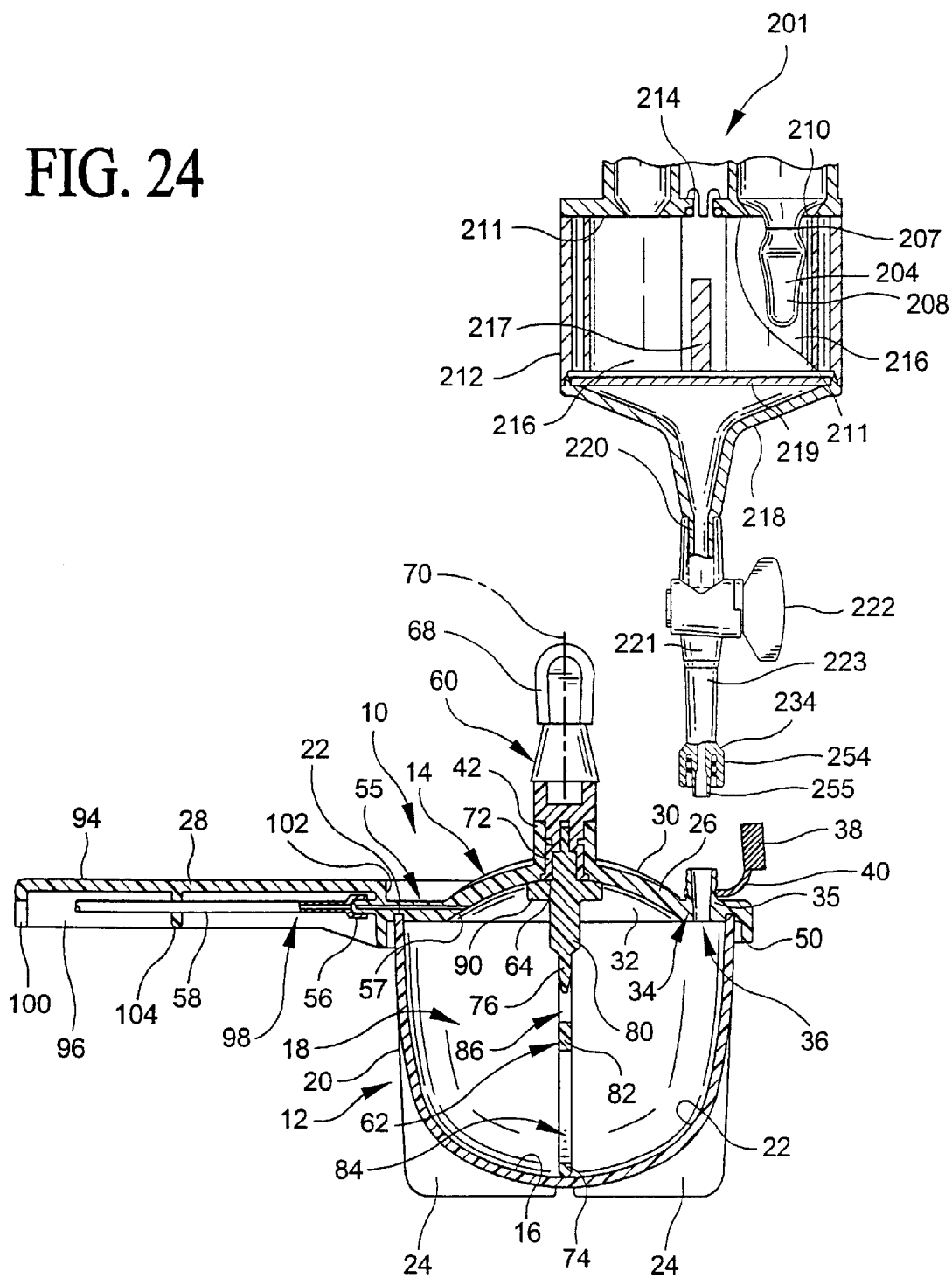
FIG. 24 is a fragmentary cross sectional view showing the monomer delivery device of the present invention being advanced in the general direction of the monomer delivery port of the cement mixing apparatus of the present invention.

In particular, as shown in FIG. 24, the port cap 38 is removed from the body 35 of the luer lock 34. Thereafter, if desirable to introduce the monomer in the presence of a vacuum within the bowl 12, the vacuum pump 14 is activated thereby generating such a vacuum within the bowl 12 in order to expel air from the cavity 18 out through vacuum outlet 56 and tube 58. In some cases, it may be desirable to generate a vacuum in cavity 18 of about 0.67 to 0.73 bar, just below the boiling point of the monomer creating the maximum vacuum pressure in the bowl 12 without the monomer boiling. However, in certain applications, it may be desirable to introduce the liquid monomer into the bowl 12 without the presence of a vacuum within the bowl 12. In particular, in certain situations, it has been observed that the introduction of monomer into the bowl 12 under a vacuum may increase the likelihood of "splashing" powder onto the walls of the cavity 18 thereby rendering mixing of the bone cement more difficult.

Figure 25:
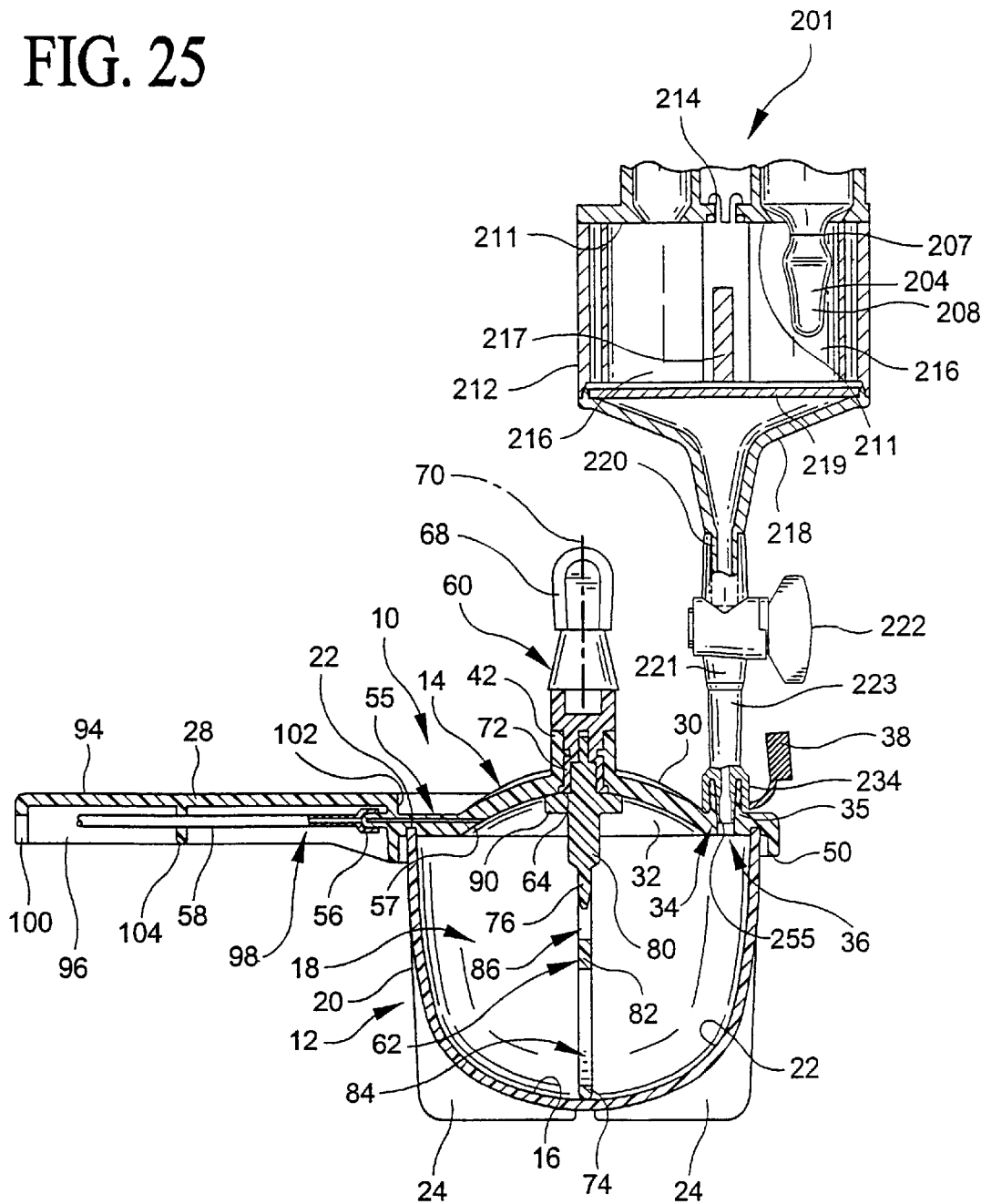
FIG. 25 is a fragmentary cross sectional view showing the monomer delivery device of the present invention sealingly secured to the monomer delivery port of the cement mixing apparatus of the present invention.

In either event, in order to deliver the liquid bone cement component (e.g. the monomer) into the cavity 18 of the bowl 12, the luer 234 from the monomer delivery device 201 is inserted into the delivery port 36 of the body 35 to form a sealed connection. In particular, as shown in FIGS. 24 and 25, a skirt portion 254 of the luer coupling 234 is advanced around the body 35 of the delivery port 36 such that an outlet tube 255 of the luer coupling 234 is sealing received into the passageway of the delivery port 36.

Once the luer coupling 234 is sealingly secured to the delivery port 36 of the mixing device, the liquid monomer may be advanced into the bowl 12. In particular, if the ampules 204 have not yet been broken, the collar 212 may be rotated such that the blades 216, 217 break the ampules 204 in the manner described above. This causes monomer to flow out of the ampules and into the cavity 18 of the bowl via a fluid path which includes the funnel 218, the spout 220, the valve 221 (when positioned in its open valve position), the luer coupling 34, and the delivery port 36 of the mixing apparatus 10.

It should be appreciated that the in certain cases, it may be desirable to break the ampules 204 prior to securing the monomer delivery device 201 to the mixing apparatus. Use of the valve 221 facilitates such early breaking of the ampules 204. In particular, the valve 221 may be positioned in its closed valve position in order to prevent the monomer from flowing therethrough. Thereafter, the ampules 204 may be broken thereby allowing the monomer to collect in the funnel 218. The monomer delivery device 201 may then be sealingly secured to the mixing apparatus 10 in the manner previously described. Once done, the valve 221 may be positioned in its open valve position in order to allow the liquid monomer collected in the funnel 218 to be advanced into the cavity 18 of the mixing apparatus 10 via the fluid path previously discussed.

After the requisite quantity of the liquid monomer has been advanced into the bowl 12, the luer coupling 234 of the monomer delivery device 201 is disengaged or otherwise removed from the delivery port 36 of the mixing apparatus 10. Note that in order to prevent any residual monomer from advancing out of the delivery device 201, the valve 221 may be positioned in its closed valve position prior to removal thereof. Once the luer coupling 234 has been spaced apart from the delivery port 36, the luer cap 38 is immediately fitted into delivery port 36, as shown by arrow 111 in FIG. 2 so as to seal the delivery port 36 and hence the cavity 18 of the bowl 12. It should be appreciated that the vacuum pump 92 may be operated to expel from the mixing apparatus 10 any monomer vapors generated by the deposition of the monomer into the bowl 12.

Once the monomer delivery device 201 has been removed from the mixing apparatus 10 in the manner described, the operator grips the handle 28 with one hand while gripping the knob 68 on crank 60 with the other hand. The operator then rotates the crank 60 about the longitudinal axis 70 of the shaftway 44. Such rotation of the crank 60 causes the body 74 and the vane 82 of the blade 62 to begin rotating within the bowl 12 thereby shearing and mixing the powder bone cement component with the liquid bone cement component (e.g. the monomer).

One illustrative mixing time for efficient mixing of the mixture is about 45 to 60 seconds. It is preferable that the vacuum remains evacuating vapors from the mixture for about an additional 15 to 20 seconds after mixing has been completed to remove any excess air or monomer vapor from the bone cement mixture. The lid 14 may then be rotated on the bowl 12 in the general direction of arrow 108 in order to remove the lid 14, as previously discussed. The operator may then use the spatula 110 (see FIG. 8) to scrape the wet bone cement out from the bowl 12. The wet bone cement can then be placed into a bone cement dispensing device (not shown) to be applied to a prosthesis.

Hence, as described herein, bone cement mixing apparatus 10 and the monomer delivery device 201 of the present invention provide numerous advantages over heretofore designed surgical assemblies. For example, the sealed relationship between the delivery device 201 and the mixing apparatus 10 provides for delivery and mixing of the bone cement without exposing the operator of the system to monomer vapors.

While the invention has been illustrated and described in detail in the drawings and foregoing description, such an illustration and description is to be considered as exemplary and not restrictive in character, it being understood that only the preferred embodiments have been shown and described and that all changes and modifications that come within the spirit of the invention are desired to be protected.

There are a plurality of advantages of the present invention arising from the various features of the surgical assembly and associated method described herein. It will be noted that alternative embodiments of the surgical assembly and associated method of the present invention may not include all of the features described yet still benefit from at least some of the advantages of such features. Those of ordinary skill in the art may readily devise their own implementations of a surgical assembly and associated method that incorporate one or more of the features of the present invention and fall within the spirit and scope of the present invention as defined by the appended claims.

What is claimed is:

1. An apparatus for preparing bone cement from a powder bone cement component and a liquid bone cement component, said apparatus a bowl;

a lid removably secured to said bowl, said lid having sealable liquid delivery port defined therein;

a crank rotatably attached to said lid;

a blade positioned in said bowl, said blade being secured to said crank such that rotation of said crank causes rotation of said blade; and a liquid delivery device having an outlet coupling which is removably securable to said liquid delivery port of said lid, wherein said lid further has a vacuum inlet defined therein, wherein said vacuum inlet is adapted to fluidly couple said bowl to a vacuum, and wherein said vacuum inlet is distinct from said liquid delivery port.

2. The apparatus of claim 1, further comprising a port cap, wherein said port cap is configured to seal said liquid delivery port when said outlet coupling of said liquid delivery device is spaced apart from said liquid delivery port.

3. The apparatus of claim 2, wherein said port cap is configured to be sealing advanced into said liquid delivery port when said outlet coupling of said liquid delivery device is spaced apart from said liquid delivery port.

4. The apparatus of claim 1, wherein said lid has a handle integrally formed therewith.

5. The apparatus of claim 1, wherein:

said lid includes a lid body, said lid body is configured to be secured to a periphery of said bowl, and said liquid delivery port is defined in said lid body.

6. An apparatus for preparing bone cement from a powder bone cement component and a liquid bone cement component, said apparatus comprising:

a bowl;

a lid removably secured to said bowl, said lid having a sealable liquid delivery port defined therein;

a crank rotatably attached to said lid;

a blade positioned in said bowl, said blade being secured to said crank such that rotation of said crank causes rotation of said blade; and a liquid delivery device having an outlet coupling which is removably securable to said liquid delivery port of said lid, wherein said outlet coupling of said liquid delivery device has a valve associated therewith, wherein said valve has an open valve position and a closed valve position, and wherein said liquid bone cement component is advanced from said liquid delivery device into said bowl through said liquid delivery port when (i) said outlet coupling of said liquid delivery device is sealingly secured to said liquid delivery port, and (ii) said valve is positioned in said open valve position.

7. The apparatus of claim 2, wherein said liquid bone cement component is prevented from advancing into said bowl through said liquid delivery port when said valve is positioned in said closed valve position.

8. A surgical assembly for mixing a liquid bone cement component with a powder bone cement component, said surgical assembly comprising:

a mixing device having (i) a bowl, (ii) a lid removably secured to said bowl, said lid having a sealable liquid delivery port defined therein, (iii) a crank rotatably attached to said lid, and (iv) a blade positioned in said bowl, said blade being secured to said crank such that rotation of said crank causes rotation of said blade;

a liquid delivery device having (i) a liquid storage container for storing said liquid bone cement component, and (ii) an outlet coupling sealingly secured to said liquid delivery port of said mixing device; and a vacuum;

wherein said liquid bone cement is advanced from said liquid storage container of said liquid delivery device into said bowl of said mixing device via a fluid path which includes said outlet coupling and said liquid delivery port, wherein said lid of said mixing device further has a vacuum inlet defined therein, wherein said vacuum inlet fluidly couples said bowl to said vacuum, and wherein said vacuum inlet is distinct from said liquid delivery port.

9. The surgical assembly of claim 8, wherein:

said mixing device further has a port cap, and said port cap is configured to seal said liquid delivery port of said lid when said outlet coupling of said liquid delivery device is spaced apart from said liquid delivery port of said lid.

10. The surgical assembly of claim 9, wherein said port cap of said mixing device is configured to be sealing advanced into said liquid delivery port of said lid when said outlet coupling of said liquid delivery device is spaced apart from said liquid delivery port of said lid.

11. The surgical assembly of claim 8, wherein said lid of said mixing device has a handle integrally formed therewith.

12. The surgical assembly of claim 8, wherein:

said lid of said mixing device includes a lid body, said lid body is configured to be secured to a periphery of said bowl of said mixing device, and said liquid delivery port is defined in said lid body.

13. A surgical assembly for mixing a liquid bone cement component with a powder bone cement component, said surgical assembly comprising:

a mixing device having (i) a bowl, (ii) a lid removably secured to said bowl, said lid having a sealable liquid delivery port defined therein, (iii) a crank rotatably attached to said lid, and (iv) a blade positioned in said bowl, said blade being secured to said crank such that rotation of said crank caused rotation of said blade; and a liquid delivery device having (i) a liquid storage container for storing said liquid bone cement component, and (ii) an outlet coupling sealingly secured to said liquid delivery port of said mixing device, wherein said liquid bone cement is advanced from said liquid storage container of said liquid delivery device into said bowl of said mixing device via a fluid path which includes said outlet coupling and said liquid delivery port, wherein said liquid delivery device further has a valve, wherein said valve is fluidly interposed between said liquid storage container and said outlet coupling, wherein said valve has an open valve position and a closed valve position, and wherein said liquid bone cement component is advanced from said liquid storage container of said liquid delivery device into said bowl of said mixing device via said fluid path when said valve is positioned in said open valve position.

14. The surgical assembly of claim 13, wherein said liquid bone cement component is prevented from advancing into said bowl of said mixing device via said fluid path when said valve is positioned in said closed valve position.

* * * * *